(12) United States Patent
Nakamura et al.

(10) Patent No.: US 10,245,291 B2
(45) Date of Patent: Apr. 2, 2019

(54) LIPID METABOLISM AND/OR SUGAR METABOLISM IMPROVER CONTAINING LACTIC ACID BACTERIUM OR TREATMENT PRODUCT THEREOF

(71) Applicant: ASAHI GROUP HOLDINGS, LTD., Sumida-Ku, Tokyo (JP)

(72) Inventors: Futoshi Nakamura, Kanagawa (JP); Nobuhisa Ashida, Kanagawa (JP); Yu Ishida, Kanagawa (JP); Shigeru Fujiwara, Kanagawa (JP)

(73) Assignee: Asahi Group Holdings, Ltd., Tokyo (JP)

( * ) Notice: Subject to any disclaimer, the term of this patent is extended or adjusted under 35 U.S.C. 154(b) by 0 days.

(21) Appl. No.: 15/408,722

(22) Filed: Jan. 18, 2017

(65) Prior Publication Data

US 2017/0119828 A1 May 4, 2017

Related U.S. Application Data

(62) Division of application No. 14/363,150, filed as application No. PCT/JP2012/081597 on Dec. 6, 2012.

(30) Foreign Application Priority Data

Dec. 7, 2011 (JP) ................................ 2011-268313
Mar. 23, 2012 (JP) ................................ 2012-067187

(51) Int. Cl.
| | |
|---|---|
| *A61K 35/745* | (2015.01) |
| *A61K 35/747* | (2015.01) |
| *C12N 1/20* | (2006.01) |
| *C12R 1/225* | (2006.01) |
| *A23L 2/52* | (2006.01) |
| *A23L 33/135* | (2016.01) |

(52) U.S. Cl.
CPC ............. *A61K 35/747* (2013.01); *A23L 2/52* (2013.01); *A23L 33/135* (2016.08); *A61K 35/745* (2013.01); *C12N 1/20* (2013.01); *C12R 1/225* (2013.01); *A23V 2002/00* (2013.01); *A23Y 2220/05* (2013.01); *A23Y 2220/37* (2013.01)

(58) Field of Classification Search
CPC ....................................................... C12N 1/20
See application file for complete search history.

(56) References Cited

U.S. PATENT DOCUMENTS

| | | |
|---|---|---|
| 5,895,648 A | 4/1999 | Cavaliere Vesely et al. |
| 2010/0021445 A1 | 1/2010 | Kawakami et al. |
| 2010/0129333 A1 | 5/2010 | Kawakami et al. |
| 2013/0089633 A1 | 4/2013 | Nakamura et al. |

FOREIGN PATENT DOCUMENTS

| | | |
|---|---|---|
| CN | 101616680 A | 12/2009 |
| EP | 0181170 A2 | 5/1986 |
| EP | 1930018 A1 | 6/2008 |
| EP | 2923704 A1 | 9/2015 |
| JP | 61-109729 A | 5/1986 |
| JP | 61-271223 A | 12/1986 |
| JP | 10-130160 A | 5/1998 |
| JP | 10-286078 A | 10/1998 |
| JP | 2003-306436 A | 10/2003 |
| JP | 2006-500378 A | 1/2006 |
| JP | 3777296 B2 | 5/2006 |
| JP | 2007-077054 A | 3/2007 |
| JP | 2007-504285 A | 3/2007 |
| JP | 2007-284360 A | 11/2007 |
| JP | 2008-024680 A | 2/2008 |
| JP | 2008-214253 A | 9/2008 |
| JP | 4336992 B2 | 9/2009 |
| WO | WO 2004/017896 A2 | 3/2004 |
| WO | WO 2004/066963 A3 | 8/2004 |
| WO | WO 2007/138993 A1 | 12/2007 |
| WO | WO 2011/066659 A1 | 6/2011 |
| WO | WO 2011/155518 A1 | 12/2011 |

OTHER PUBLICATIONS

Esposito et al., "Probiotics Reduce the Inflammatory Response Induced by a High-Fat Diet in the Liver of Young Rats," J. Nutr., 2009, 139(5):905-911.
Kondo et al., "Antiobesity Effects of *Bifidobacterium breve* Strain B-3 Supplementation in a Mouse Model with High-Fat Diet-Induced Obesity," Biosci. Biotechnol. Biochem., 2010, 74(8):1656-1661.
Sawada et al., "Stress Relief Effect of *Lactobacillus gasseri* Strain CP2305," Journal of Intestinal Mibrobiology (Intestinal Bacteria Magazine), Apr. 2009, 23(2):96, with English translation, 2 pages.
Segawa et al., "Oral administration of heat-killed *Lactobacillus brevis* SBC8803 ameliorates alcoholic liver disease in ethanol-containing diet-fed C57BL/6N mice," International Journal of Food Microbiology, 2008, 128:371-377.
Supplementary European Search Report dated Jun. 19, 2015, in EP 12855562.0.
Marion-Letellier et al., "Dietary modulation of peroxisome proliferator-activated receptor gamma," Gut, Apr. 1, 2009, 58(4):586-593.
Office Action dated May 3, 2016, in KR 10-2014-7018122.
Namba et al., "Effect of Oral Administration of Lysozyme or Digested Bacterial Cell Walls on Immunostimulation in Guinea Pigs," Infection and Immunity, Feb. 1981, 31(2):580-583.

(Continued)

*Primary Examiner* — Bin Shen
(74) *Attorney, Agent, or Firm* — Foley & Lardner LLP

(57) ABSTRACT

This invention provides the use of a microorganism capable of improving both lipid metabolism and sugar metabolism. Specifically, the invention relates to: a lipid metabolism and/or sugar metabolism improver comprising, as an active ingredient, a bacterial cell selected from bacteria belonging to the genus *Lactobacillus* and the genus *Bifidobacterium*, a treated product of the bacterial cell, or a mixture thereof, having dual-agonistic activities to peroxisome proliferator activated receptor (PPAR)α and peroxisome proliferator activated receptor (PPAR)γ; to a food or a beverage comprising the improver; and to a pharmaceutical composition comprising the improver.

10 Claims, 4 Drawing Sheets

(56) References Cited

OTHER PUBLICATIONS

Tursi et al., "Balsalazide and/or high-potency probiotic mixture (VSL#3) in maintaining remission after attack of acute, uncomplicated diverticulitis of the colon," Int. J. Colorectal Dis., 2007, 22:1103-1108.
Temmerman et al., "Culture-Independent Analysis of Probiotic Products by Denaturing Gradient Gel Electrophoresis," Applied and Environmental Microbiology, Jan. 2003, 69(1):220-226.
Office Action dated Oct. 18, 2016, in CN 201280059978.4.
Office Action dated Dec. 20, 2016, in JP 2015-017278.
Lee et al., "Activation of peroxisome proliferator-activated receptor-α enhances fatty acid oxidation in human adipocytes," Biochemical and Biophysical Research Communications, 2011, 407:818-822.
Lenhard et al., "Effects of Troglitazone and Metformin on Glucose and Lipid Metabolism," Biochemical Pharmacology, 1997, 54:801-808.
Office Action dated Mar. 14, 2017, in JP 2015-017278.
Brooks et al., "Design and Synthesis of 2-Methyl-2-{4-[2-(5-methyl-2-aryloxazol-4-yl)ethoxylphenoxy}propionic Acids: A New Class of Dual PPARα/γ Agonists," J. Med. Chem., 2001, 44:2061-2064.
Lohray et al., "(-)3[4[2-(Phenoxazin-10-yl)ethoxy]phenyl]-2-ethoxypropanoic Acid [(-)DRF 2725]: A Dual PPAR Agonist with Potent Antihyperglycemic and Lipid Modulating Activity," J. Med. Chem., 2001, 44:2675-2678.
Office Action dated Dec. 20, 2017, in EP 12855562.0.

LIPID METABOLISM AND/OR SUGAR METABOLISM IMPROVER CONTAINING LACTIC ACID BACTERIUM OR TREATMENT PRODUCT THEREOF

CROSS-REFERENCE TO RELATED APPLICATIONS

This application is a Divisional of U.S. application Ser. No. 14/363,150, now abandoned, which is the U.S. National Stage application of PCT/JP2012/081597, filed Dec. 6, 2012, which claims priority from Japanese application nos. JP 2011-268313, filed Dec. 7, 2011, and JP 2012-067187, filed Mar. 23, 2012.

TECHNICAL FIELD

The present invention relates to a lipid metabolism and/or sugar metabolism improver comprising a bacterial cell of the genus *Lactobacillus* or the genus *Bifidobacterium* or a treated product thereof having a high ability to activate Peroxisome Proliferator Activated Receptors (PPARs) α and γ, which are deeply involved with metabolic syndrome. The present invention also relates to a functional food or a pharmaceutical composition comprising such a lipid metabolism and/or sugar metabolism improver for treating or preventing diseases or disorders associated with the lipid metabolism and sugar metabolism.

BACKGROUND ART

In recent years, more and more people have metabolic syndrome or are candidates thereof. Metabolic syndrome is defined as multiplex conditions of visceral fat type obesity in combination with hyperlipidemia, hyperglycemia, hypertension, and the like, and has a high risk of developing arteriosclerotic diseases. To improve the metabolic syndrome, PPARs associated with the lipid and sugar metabolisms are attracting attentions. PPARs are nuclear transcriptional regulators. PPARα that is highly expressed mostly in the liver and small intestine causes fat burning by promoting the β oxidation of fatty acids and also exhibits the action of promoting HDL cholesterol production. PPARγ, highly expressed mostly in fat tissues, improves the insulin resistance by regulating the fat cell differentiation in the fatty tissues, suppressing the secretion of an inflammation factor TNF-α from fat cells, and promoting the secretion of adiponectin.

A fibrate preparation which is a PPARα ligand agent and a thiazolidin derivative which is a PPARγ ligand agent are known as pharmaceutical products for activating PPARs, but adverse effects thereof are concerned when taken for an extended period of time.

On the other hand, it is documented that bacterial cells of lactic acid bacteria or *Bifidobacteria* and cultured products thereof (culture broth, culture supernatant, concentrated products thereof, and the like) are effective for improving the lipid metabolism, for example, reducing blood cholesterol, reducing body fat or visceral fat, or the like (e.g., Patent Documents 1 to 4). However, they did not activate PPARs or did not have satisfactory effects. It is also reported that an organic solvent extract of a lactic acid bacterium activates PPAR (Patent Document 5) but this was only to show the activity of PPARα, and the effect thereof was not sufficient, either. Further, it is reported that the activity of liver PPARα in a model mouse with alcoholic liver disease was examined when *Lactobacillus* brevis SBC8803 strain was administered to the mouse, and, as a result, the activation remained unchanged (Non Patent Document 1), and it is documented when a mixture of a plurality of lactic acid bacteria was administered to a steatohepatitis model which was on a high fat diet, the PPARα activity whose expression had been reduced due to the high fat diet was recovered (Non Patent Document 2), but no descriptions regarding PPARγ are found. To enhance the treatment and prevention efficiency of the metabolic syndrome, a material capable of activating both PPARα and PPARγ (dual-agonist) is desired.

PRIOR ART DOCUMENT

Patent Document

Patent Document 1: Japanese Patent Publication (Kokai) No. 2008-24680
Patent Document 2: Japanese Patent No. 4336992
Patent Document 3: Japanese Patent Publication (Kokai) No. 2003-306436
Patent Document 4: Japanese Patent No. 3777296
Patent Document 5: Japanese Patent Publication (Kokai) No. 2007-284360

Non-Patent Document

Non Patent Document 1: Int. J. Food Microbiol. 128(2): 371-377, 2008
Non Patent Document 2: J. Nutr. 139(5): 905-911, 2009

SUMMARY OF THE INVENTION

Problem to be Solved by the Invention

An object of the present invention is to provide a means which has a highly agonistic activation of both PPARα and PPARγ and is effective and safe for improving both lipid metabolism and/or sugar metabolism.

Another object of the present invention is to provide a means for treating or preventing diseases or disorders associated with lipid metabolism disorders and/or sugar metabolism disorders.

Means for Solving Problem

The present inventors carried out extensive studies to solve the above problems and have now accidentally found that a plurality of lactic acid bacteria strains or *Bifidobacteria* strains, which strongly activate both PPARα and PPARγ. In particular, *Lactobacillus amylovorus* CP1563 strain has now been found as the highly active strains.

Accordingly, the present invention encompasses the following embodiments.

(1) A bacterial cell or a treated product thereof having dual-agonistic activities on a peroxisome proliferator activated receptor (PPAR)α and a peroxisome proliferator activated receptor (PPAR)γ.

(2) The bacterial cell or the treated product thereof according to the above (1), wherein the PPARα activity is 70 or more relative to negative control activity of 0 and positive control activity of 100 as measured by PPARα reporter assay and the PPARγ ligand activity shows positive exceeding 0 relative to negative control activity of 0 and positive control activity of 100 as measured by PPARγ reporter assay.

(3) The bacterial cell or the treated product thereof according to the above (1) or (2), wherein the bacterial cell belongs to *Lactobacillus amylovorus, Lactobacillus gasseri, Bifidobacterium infantis, Bifidobacterium adolescentis*, or *Bifidobacterium breve*.

(4) The bacterial cell or the treated product thereof according to any one of the above (1) to (3), wherein the bacterial cell is the CP1563 strain (Accession Number FERM BP-11255) or CP1562 strain (Accession Number FERM BP-11379) or a mutant or bred strain thereof, or a mutant or bred strain of CP2305 strain (Accession Number FERM BP-11331).

(5) The treated product of bacterial cell according to any one of the above (1) to (4), which is a destructed product of the bacterial cell, an extracted product of the bacterial cell, or a dried product thereof.

(6) A lipid metabolism and/or sugar metabolism improver comprising, as an active ingredient, a bacterial cell, a treated product thereof, or a mixture thereof having dual-agonistic activities on a peroxisome proliferator activated receptor (PPAR)α and a peroxisome proliferator activated receptor (PPAR)γ, wherein the bacterial cell is preferably selected from the genus *Lactobacillus* and the genus *Bifidobacterium*.

(7) A lipid metabolism and/or sugar metabolism improver comprising, as an active ingredient, a bacterial cell selected from bacteria belonging to the genus *Lactobacillus* and the genus *Bifidobacterium*, a treated product thereof, or a mixture thereof having dual-agonistic activities on a peroxisome proliferator activated receptor (PPAR)α and a peroxisome proliferator activated receptor (PPAR)γ.

(8) The lipid metabolism and/or sugar metabolism improver according to the above (6) or (7), wherein the PPARα activity is 70 or more relative to negative control activity of 0 and positive control activity of 100 as measured by PPARα reporter assay and the PPARγ ligand activity shows positive exceeding 0 relative to negative control activity of 0 and positive control activity of 100 as measured by PPARγ reporter assay.

(9) The lipid metabolism and/or sugar metabolism improver according to any one of the above (6) to (8), wherein the bacterial cell belongs to *Lactobacillus amylovorus, Lactobacillus gasseri, Bifidobacterium infantis, Bifidobacterium adolescentis*, or *Bifidobacterium breve*.

(10) The lipid metabolism and/or sugar metabolism improver according to any one of the above (6) to (9), wherein the bacterial cell is *Lactobacillus amylovorus* CP1563 strain (Accession Number FERM BP-11255) or *Lactobacillus amylovorus* CP1562 strain (Accession Number FERM BP-11379) or *Lactobacillus gasseri* CP2305 strain (Accession Number FERM BP-11331), or a mutant or bred strain thereof.

(11) The lipid metabolism and/or sugar metabolism improver according to any one of the above (6) to (10), wherein the treated product of bacterial cell is a destructed product of the bacterial cell, an extracted product of the bacterial cell, or a dried product thereof.

(12) The lipid metabolism and/or sugar metabolism improver according to any one of the above (6) to (11), which further comprises a carrier or an excipient used for foods or beverages or pharmaceutical drugs.

(13) A food or beverage comprising the lipid metabolism and/or sugar metabolism improver according to any one of the above (6) to (12) as a food additive.

(14) The food or beverage according to the above (13), which is a functional food or health food for use in improving the lipid metabolism and/or sugar metabolism.

(15) A pharmaceutical composition for use in preventing, improving, or treating a lipid metabolism disorder and/or sugar metabolism disorder, comprising as an active ingredient the lipid metabolism and/or sugar metabolism improver according to any one of the above (6) to (12).

(16) A process for producing a food or beverage having a lipid metabolism and/or sugar metabolism improving effect, comprising adding the lipid metabolism and/or sugar metabolism improver according to any one of the above (6) to (12) to a food or beverage.

(17) Use of *Lactobacillus amylovorus* CP1563 strain (Accession Number FERM BP-11255), *Lactobacillus amylovorus* CP1562 strain (Accession Number FERM BP-11379), *Lactobacillus gasseri* CP2305 strain (Accession Number FERM BP-11331), or a mutant or bred strain thereof, a treated product thereof, or a mixture thereof in the production of the lipid metabolism and/or sugar metabolism improver according to any one of the above (6) to (12).

(18) *Lactobacillus amylovorus* CP1563 strain (Accession Number FERM BP-11255) or *Lactobacillus amylovorus* CP1562 strain (Accession Number FERM BP-11379), or a mutant or bred strain thereof, or a mutant or bred strain of *Lactobacillus gasseri* CP2305 strain (Accession Number FERM BP-11331) for use in imparting a lipid metabolism and sugar metabolism improving effect.

(19) *Lactobacillus amylovorus* CP1563 strain (Accession Number FERM BP-11255) or *Lactobacillus amylovorus* CP1562 strain (Accession Number FERM BP-11379) or a mutant or bred strain thereof, or a mutant or bred strain of *Lactobacillus gasseri* CP2305 strain (Accession Number FERM BP-11331).

(20) The bacterial cell or the treated product thereof according to the above (1) or (2), wherein the bacterial cell belongs to the genus *Lactobacillus* or the genus *Bifidobacterium*.

(21) Use of the bacterial cell or the treated product thereof according to any one of the above (1) to (5) for use in the production of a composition for improving lipid metabolism and/or sugar metabolism.

(22) Use of the bacterial cell or the treated product thereof according to any one of the above (1) to (5) for use in the production of a composition for preventing lipid metabolism and/or sugar metabolism.

(23) The bacterial cell or the treated product thereof according to any one of the above (1) to (5) for use in the production of a composition for improving lipid metabolism and/or sugar metabolism.

(24) The bacterial cell or the treated product thereof according to any one of the above (1) to (5) for use in the production of a composition for preventing lipid metabolism and/or sugar metabolism.

(25) The bacterial cell or the treated product thereof according to any one of the above (1) to (5) for use in the production of a composition for reducing subcutaneous fat and/or visceral fat.

(26) The bacterial cell or the treated product thereof according to any one of the above (1) to (5) for use in the production of a composition for preventing accumulation of subcutaneous fat and/or visceral fat.

The present invention encompasses the contents described in the specifications and/or drawings of Japanese Patent Application Nos. 2011-268313 and 2012-067187, to which the present application claims priority.

According to the present invention, when bacterial cells such as *Lactobacillus amylovorus, Lactobacillus gasseri*, or the like, comprising *Lactobacillus amylovorus* CP1563 strain, *Lactobacillus amylovorus* CP1562 strain, *Lactobacillus gasseri* CP2305 strain, and the like, or a treated product thereof, which have dual-agonist activities to both PPARα and PPARγ, are taken, fat burning and HDL cholesterol production are promoted and the lipid metabolism is improved by strong activation of PPARα, and further the sugar metabolism and the insulin resistance are improved by activation of PPARγ, whereby the metabolic syndrome can be prevented or improved.

MODE FOR CARRYING OUT THE INVENTION

Figure 1:
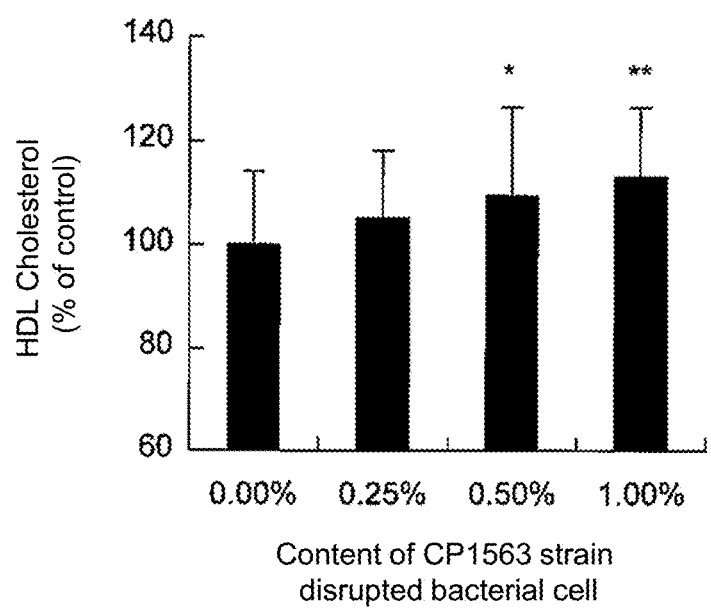
FIG. 1 is a graph showing a dose dependent effect (on HDL-cholesterol) of a lactic acid bacterium in diet induced obese model. * and ** show the statistical significance.

Hereinafter, the present invention will be described in more detail.

1. Lipid Metabolism and/or Sugar Metabolism Improver

According to the first aspect, the present invention provides a fat metabolism and/or sugar metabolism improver comprising, as an active ingredient, preferably a bacterial cell of a lactic acid producing bacterium, more preferably a bacterial cell selected from the genus *Lactobacillus* and the genus *Bifidobacterium*, a treated product thereof, or a mixture thereof having dual-agonist activities to peroxisome proliferator activated receptor (PPAR)α and peroxisome proliferator activated receptor (PPAR)γ.

The present invention also provides the above-mentioned bacterial cell or treated product thereof as described below.

The "PPARα agonist activity" used herein promotes the fat burning and the HDL cholesterol production and improves the fat metabolism. When the activity is enhanced, diseases such as hyperlipidemia, dyslipidemia, obesity, hypercholesterolemia, hypertriglyceridemia, arteriosclerosis, inflammatory symptoms, and the like, can be prevented, improved or treated.

The "PPARγ agonist activity" used herein suppresses the secretion of the inflammation factor TNF-α from fat tissues and promotes the secretion of adiponectin, thereby improving both of the insulin resistance and the sugar metabolism. When the activity is enhanced, diseases such as hyperglycemia, non-insulin-dependent diabetes mellitus, arteriosclerosis, cardiac hypertrophy, ischemic heart disease, or the like, can be prevented, improved or treated.

The fat metabolism and/or sugar metabolism improver of the present invention is also effective for preventing, improving or treating so-called the metabolic syndrome including obesity and diabetes by having both PPARα agonist activity and PPARγ agonist activity.

The PPARα agonist activity in the lipid metabolism and/or sugar metabolism improver of the present invention is a positive activity of typically 70 or more, preferably 80 or more, further preferably 90 or more, most preferably 100 or more, for example, 110 or more, 120 or more, 130 or more, or 140 or more, relative to negative control activity of 0 and positive control activity of 100 as measured by PPARα reporter assay (see Examples later).

The negative control activity of 0 and positive control activity of 100 as measured by PPARα reporter assay used herein is defined in Definition 1 to be described later.

The PPARγ agonist activity in the lipid metabolism and/or sugar metabolism improver of the present invention is a positive activity of exceeding 0, for example, 2 or more, 4 or more, 5 or more, preferably 10 or more, 20 or more, further preferably 30 or more, 35 or more, most preferably 40 or more, relative to negative control activity of 0 and positive control activity of 100 as measured by PPARγ reporter assay (see Examples later).

The negative control activity of 0 and positive control activity of 100 as measured by PPARγ reporter assay used in the present invention is defined in Definition 2 to be described later.

According to the present invention, the bacterial cell having the dual-agonistic activities to PPARα and PPARγ is a bacterial cell selected from bacteria belonging to the genus *Lactobacillus* and the genus *Bifidobacterium*, a treated product thereof, or a mixture thereof.

Such a bacterial cell includes, but is not limited to, *Lactobacillus amylovorus, Lactobacillus gasseri, Bifidobacterium infantis, Bifidobacterium adolescentis, Bifidobacterium breve, Bifidobacterium bifidum, Bifidobacterium longum, Bifidobacterium pseudocatenulatum, Bifidobacterium lactis, Bifidobacterium animalis, Bifidobacterium pseudolongum, Bifidobacterium magnum, Lactobacillus acidophilus, Lactobacillus casei, Lactobacillus paracasei, Lactobacillus rhamnosus, Lactobacillus helveticus, Lactobacillus fermentum, Lactobacillus brevis, Lactobacillus plantarum, Lactobacillus salivarius, Lactobacillus reuteri, Lactobacillus johnsonii, Lactobacillus jensenii, Lactobacillus crispatus, Lactobacillus delbrueckii, Lactobacillus zeae, Lactobacillus gallinarum*, mutants thereof, or bred strains thereof.

Preferable cell strains are *Lactobacillus amylovorus* strains (e.g., CP1563 strain; Accession Number FERM BP-11255, CP1562 strain; Accession Number FERM BP-11379), *Lactobacillus gasseri* strains (e.g., CP2305 strain; Accession Number FERM BP-11331), *Bifidobacterium infantis* strains, *Bifidobacterium breve* strains, or mutants or bred strains thereof, and most preferable strains are CP1563 strain (Accession Number FERM BP-11255) or mutants or bred strains thereof. *Lactobacillus amylovorus* CP1563 strain and *Lactobacillus amylovorus* CP1562 strain are lactic acid bacteria derived from the human intestinal tract. These bacterial strains or treated products thereof are validated to have the fat metabolism and/or sugar metabolism improving action in Examples later, and available from the National Institute of Advanced Industrial Science and Technology, International Patent Organism Depositary (1-1-1 Higashi, Tsukuba, Ibaraki, Tsukuba Central 6, 305-8566 Japan).

The lactic acid producing bacteria usable in the present invention, preferably bacterial species selected from the genus *Lactobacillus* and the genus *Bifidobacterium*, can be grown and recovered by incubating under typically employed conditions using media commonly used for incubating bacterial species such as *Lactobacillus* (a lactic acid bacterium) and *Bifidobacterium*.

A culture medium typically contains a carbon source, a nitrogen source, inorganic salts, and the like, and may be a natural medium or synthetic medium as long as it can efficiently incubate the above bacterial species. Examples of the usable carbon source include lactose, glucose, sucrose, fructose, galactose, molasses, and the like; examples of the usable nitrogen source include organic nitrogen-containing products such as casein hydrolysate, whey protein hydrolysate, soy protein hydrolysate, yeast extract, meat extract, and the like. Examples of the inorganic salts include phosphate, sodium, potassium, magnesium, manganese, iron, zinc, and the like. Examples of suitable media for culturing lactic acid bacteria include MRS liquid medium, GAM medium, BL medium, Briggs Liver Broth, animal milk, skim milk, milk whey, and the like. Preferably, sterilized MRS medium can be used. When used for food, a medium composed only of food materials and food additives can also be prepared and used. For natural media, tomato juice, carrot juice, other vegetable juices, or apple juice, pineapple juice, grape juice, or the like, can also be used.

The incubation is carried out under anaerobic conditions at 20° C. to 50° C., preferably 25° C. to 42° C., more preferably about 37° C. The temperature condition can be adjusted using an incubator, mantle heater, jacket, or the like. The anaerobic condition refers to an environment of low oxygen at which the bacterium can grow, and the anaerobic condition can be achieved by, for example, using an anaerobic chamber, anaerobic box or a sealed container or bag containing an oxygen absorber, or simply sealing a culture container. The culture mode is stationary culture, shaking culture, tank culture, or the like. The incubation time is not limited but may be, for example, 3 hours to 96 hours. The medium pH at the time of initiating incubation is preferably maintained, for example, from 4.0 to 8.0.

When *Lactobacillus amylovorus* CP1563 strain and *Lactobacillus amylovorus* CP1562 strain are used as lactic acid bacteria, they may be inoculated in food grade media for lactic acid bacteria and incubated at about 37° C. overnight (for about 18 hours).

After incubation, the obtained cultured product of a lactic acid bacterium may be used without further treatment, or may be roughly purified as necessary by the centrifugal separation and/or the solid liquid separation or sterilization procedure by filtration, or the like, may be carried out. Preferably, only the bacterial cells of lactic acid bacteria are recovered by the centrifugal separation. In addition, the lactic acid bacteria used in the present invention may be either wet bacterial cell or dry bacterial cell.

When a mutant of the bacterial strain or bacterial species selected from the genus *Lactobacillus* and the genus *Bifidobacterium* is produced, these bacterial cells are stationarily cultured in MRS medium until the logarithmic growth phase, subsequently washed in sterilized physiological saline or sterilized water, and treated with 50 to 500 μg/ml of a mutagen such as N-methyl-N'-nitro-N-Nitrosoguanidine (NTG) at 30 to 37° C. for 30 to 60 minutes in the same sterilized physiological saline or sterilized water to obtain a mutant strain. For the mutagenesis, ultraviolet rays or known mutagens such as ethylmethane sulfonate (EMS), fluorouracil (5-FU), or the like, can be used in addition to NTG, and a commonly known means may be suitably used. Taxonomically, the microbiological characteristics of an obtained bacterial strain can be verified by, for example, examining the homology of a 16S rRNA gene nucleotide sequence, examining the DNA-DNA homology by DNA-DNA hybridization with the standard strain, examining the sugar utilizing properties, or the like.

Examples of the treated product of a bacterial cell used herein include, but are not limited to, destructed products of a bacterial cell extracts of a bacterial cell, dried products, frozen products, water-dispersed products, emulsified products, or the like, thereof.

The destructed products of a bacterial cell are those obtained by the destruction treatment such as disrupting (in this case a bacterial cell disrupted product is obtained), grinding, enzymatically treating, chemically treating, dissolving, or the like, and the form of the destructed product of a bacterial cell is not limited to a specific one as long as the bacterial cell has dual-agonistic activities to peroxisome proliferator activated receptor (PPAR)α and peroxisome proliferator activated receptor (PPAR)γ. It is preferable to use those obtained by recovering the entire destructed bacterial cell (that is, the essentially all components constituting the cell) without further treatment, as, for example, those obtained by drying, such as freeze-drying, an aqueous medium in which a bacterial cell is disrupted.

The destruction of bacterial cell can be carried out, using techniques and devices known in the art, by, for example, physical disruption, enzymatic dissolution treatment, or the like. The physical disruption may be carried out in either wet mode (processed in the form of bacterial cell suspension) or dry mode (processed in the form of bacterial cell powder), and can be carried out by stirring using a homogenizer, ball mill, bead mill, DYNO-mill, Planetary mill, or the like; by compressing using a jet mill, French press, cell disruptor, or the like; or by filtering using a filter. In the enzymatic dissolution treatment, the cell wall of bacterial cell can be destructed using an enzyme such as lysozyme, or the like.

Specifically, in the method for preparing a disrupted product of the bacterial cell, the bacterial cell is disrupted by treating a suspension of a lactic acid bacterium 1 to 7 times (e.g., 3 to 5 times) in a known DYNO-MILL cell disruptor (DYNO-MILL disrupting device, or the like), using glass beads, at a circumferential speed of 10.0 to 20.0 m/s (e.g., about 14.0 m/s) and a processing flow rate of 0.1 to 10 L/10 min (e.g., about 1 L/10 min) at a disrupting tank temperature of 10 to 30° C. (e.g., about 15° C.). Alternatively, the bacterial cell is disrupted by, for example, treating a suspension of a lactic acid bacterium 1 to 30 times (e.g., 10 times) in a known wet jet mill cell disruptor (JN20 Nano Jet Pal, or the like) at a discharge pressure of 50 to 1000 MPa (e.g., 270 MPa) and a processing flow rate of 50 to 1000 (e.g., 300) ml/min. Alternatively, the bacterial cell can also be disrupted by treating lactic acid bacterium cell powder in a known dry planetary mill cell disruptor (GOT5 Galaxy 5, or the like) in the presence of various balls (e.g., 10 mm zirconium ball, 5 mm zirconium ball, 1 mm aluminum ball) at a rotation number of 50 to 10,000 rpm (e.g., 240 rpm, 190 rpm, 110 rpm) for 30 minutes to 20 hours (e.g., 5 to 10 hours). The bacterial cell may also be disrupted by treating lactic acid bacterium cell powder 1 to 10 times (e.g., 1 time) in a known dry jet mill cell disruptor (Jet O-mizer, or the like) at a supplying rate of 0.01 to 10000 g/min (e.g., 0.5 g/min) and a discharge pressure of 1 to 1000 $kg/cm^2$ (e.g., 6 $kg/cm^2$).

In the present invention, the disrupted product of a bacterial cell still shows the effect even when the bacterial cell has just a hall, but it is desirable to prepare the disrupted product so that the average major axis of destructed bacterial cells is 90% or less of before the destruction treatment. For example, when the bacterial cell is destructed by the dissolution treatment, the average major axis of destructed bacterial cells may sometimes be close to 0%. Thus, the bacterial cell can be destructed so that the average major axis of destructed bacterial cells in the disrupted product is 90% or less, preferably 80% or less, 70% or less, 60% or less, or 50% or less, more preferably 40% or less, 30% or less, or 20% or less, of before the disruption.

The bacterial cell and/or the disrupted product thereof can be dried to form a powder product or a granulated product. Specific drying methods include, but are not particularly limited to, spray-drying, drum drying, vacuum drying, freeze-drying, and the like, and these methods may be employed alone or in combination. At this time, a commonly used carrier or excipient may be added where needed.

Further, the bacterial cell extract can be obtained by extraction treatment of the bacterial cell or the disrupted product thereof with water, an organic solvent or a mixed solvent, optionally in combination, and recovering a fraction containing the active ingredient having the agonistic activities to PPARα and PPARγ. The organic solvent is a polar solvent, nonpolar solvent, or a mixed solvent thereof, and examples of the polar solvent include alcohols such as methanol, ethanol, and propanol, acetone, acetonitrile, dioxane, DMSO, DMF, and the like; examples of the nonpolar solvent include ethers such as diethyl ether, hydrocarbons such as hexane, heptane, and the like, alkyl halides such as dichloromethane, chloroform, and the like. Particularly, the active ingredient of the present invention, as described in Examples later, may have a property which is easily extracted by a nonpolar organic solvent such as diethyl ether, or the like, and may be partially extracted also by a polar organic solvent such as ethanol, acetonitrile, DMSO, or the like. The fact that the extract has the agonistic activities to PPARα and PPARγ can be confirmed by known assay techniques such as PPARα reporter assay, PPARγ reporter assay, and the like, as described in Examples later. All of the extracts obtained from the bacterial species or bacterial strains belonging to the genus *Lactobacillus* or the genus *Bifidobacterium* as exemplified above have the ability to activate PPARα and PPARγ. Of these, the extracts of *Lactobacillus amylovorus* CP1563 strain, *Lactobacillus amylovorus* CP1562 strain, *Lactobacillus gasseri* CP2305 strain, and the like, have far better ligand activities to PPARα and PPARγ. The bacterial cell extract of the present invention also encompasses concentrated products or residues obtained by concentrating using a vaporizer such as an evaporator, or the like, preferably those obtained by removing the solvent.

Furthermore, a component or a fraction having the lipid metabolism and sugar metabolism improving actions may be purified from the above disrupted product of the bacterial cell using a known separation and purification method. Examples of the separation and purification method include the method which utilizes solubility such as salt precipitation, organic solvent precipitation, and the like; the method which utilizes the molecular weight difference such as dialysis, ultrafiltration, gel filtration, and the like; the method which utilizes the electric charge difference such as ion exchange chromatography and the like; the method which utilizes the specific bonding such as affinity chromatography and the like; the method which utilizes the hydrophobicity such as hydrophobic chromatography, reversed phase chromatography, and the like; and these methods can be used alone or in combination of two or more methods.

The thus obtained bacterial cell disrupted product, bacterial cell extract, or active ingredient containing fraction can be prepared as the lipid metabolism and/or sugar metabolism improver without further treatment or in combination with a carrier or excipient used for foods or beverages or pharmaceutical drugs. If necessary, additives such as a disintegrator, binder, wetting agent, stabilizer, buffer, lubricant, preservative, surfactant, sweetener, flavor, perfume, acidulant, coloring agent, or the like, may be contained. Further, the dosage form is not limited and can be tablets, capsules, granules, powders, dusts, syrups, dry syrups, solutions, suspensions, emulsifiers, or the like.

The above bacterial cell or treated products thereof contained in the lipid metabolism and/or sugar metabolism improver of the present invention are produced from the number of bacterial cells corresponding to, but not limited to, for example, about $10^5$ cells/g to about $10^{14}$ cells/g, preferably about $10^8$ cells/g to about $10^{12}$ cell/g as the number of bacterial cell before treatment.

The lipid metabolism and/or sugar metabolism improver of the present invention comprises, as the active ingredient, the bacterial cell or the treated product thereof as described above, and the bacterial cell or the treated product thereof may be those obtained from one or a plurality of bacterial species.

Accordingly, the present invention also provides, the use of CP1563 strain (Accession Number FERM BP-11255), CP1562 strain (Accession Number FERM BP-11379), CP2305 strain (Accession Number FERM BP-11331), or a mutant or bred strain thereof, a treated product thereof, or a mixture thereof, for use in the production of the lipid metabolism and/or sugar metabolism improver of the present invention.

The present invention further provides CP1563 strain (Accession Number FERM BP-11255) or CP1562 strain (Accession Number FERM BP-11379), or a mutant or bred strain thereof, which imparts the lipid metabolism and sugar metabolism improving effects.

Herein, "FERM BP-11255" pertinent to the present invention is the accession number for *Lactobacillus amylovorus* CP1563 strain internationally deposited with the National Institute of Advanced Industrial Science and Technology, International Patent Organism Depositary (1-1-1 Higashi, Tsukuba, Ibaraki, Tsukuba Central 6 (305-8566 Japan)) on May 25, 2010 under the Budapest Treaty, "FERM BP-11379" is the accession number for *Lactobacillus amylovorus* CP1562 strain internationally deposited with the same Organism Depositary on Apr. 22, 2011 under the Budapest Treaty, and "FERM BP-11331" is the accession number for *Lactobacillus gasseri* CP2305 strain internationally deposited with the same Organism Depositary on Sep. 11, 2007 under the Budapest Treaty.

2. Food or Beverage and Pharmaceutical Composition

The present invention further provides a food or beverage which comprises the lipid metabolism and/or sugar metabolism improver of the present invention as a food additive. According to this embodiment, the food or beverage is a functional food or health food for use in improving the lipid metabolism and/or sugar metabolism.

The present invention further provides a process for producing a food or beverage having the lipid metabolism and/or sugar metabolism improving effects, which process comprises adding the lipid metabolism and/or sugar metabolism improver of the present invention to a food or beverage.

The present invention further provides a pharmaceutical composition for use in preventing, improving, or treating lipid metabolism disorders and sugar metabolism disorders, comprising the lipid metabolism and/or sugar metabolism improver of the present invention as the active ingredient.

Hereinafter, the pharmaceutical composition and the food or beverage according to the present invention are described.

When the lipid metabolism improver obtained as described above is continuously taken, the improving effects on lipid metabolism and sugar metabolism are expected to be achieved and hence the improver can be used for treating or preventing the diseases or disorders associated with the lipid metabolism and sugar metabolism. As such, the lipid metabolism and/or sugar metabolism improver can be used by adding to foods and beverages, pharmaceutical products, or the like.

When the lipid metabolism and/or sugar metabolism improver of the present invention is used in the form of a pharmaceutical composition or a food or beverage (e.g., functional food, or the like), the form of a pharmaceutical composition or a food or beverage is not limited and may be, for example, oral preparations such as tablets, capsules, granules, powders, dusts, syrups, dry syrups, solutions, suspensions, inhalants, or the like, enteral preparations such as suppositories or the like, preparation forms such as drops, injections, or the like. Of these, the oral preparations are preferable. The solution preparations such as solutions, suspensions, or the like, may be a preparation which is dissolved or suspended in water or other suitable medium immediately before taken, and the tablets and granules may have the surface coated by a well-known method. Additionally, the lipid metabolism improver of the present invention may be formulated into a preparation with the controlled release such as sustained release preparations, delayed release preparations, immediate release preparations, or the like using a technique known in the art.

Such a form can be produced in accordance with a routine method by adding, to the ingredients described above, additives commonly used such as an excipient, disintegrator, binder, wetting agent, stabilizer, buffer, lubricant, preservative, surfactant, sweetener, flavor, perfume, acidulant, coloring agent, or the like, depending on the preparation (or dosage) form. For example, when the lipid metabolism and/or sugar metabolism improver is prepared in the form of pharmaceutical composition, pharmaceutically acceptable carriers or additives can be added. Examples of the pharmaceutically acceptable carriers and additives include water, pharmaceutically acceptable organic solvents, collagen, polyvinyl alcohols, polyvinylpyrrolidone, carboxy vinyl polymers, sodium alginate, water-soluble dextran, water-soluble dextrin, sodium carboxymethyl starch, pectin, xanthan gum, gum arabic, casein, gelatin, agar, glycerol, propylene glycol, polyethylene glycol, petrolatum, paraffin, stearyl alcohol, stearic acid, human serum albumin, mannitol, sorbitol, lactose, surfactants acceptable as pharmaceutical additives, as well as artificial cell structures such as liposome, and the like.

The content of the lipid metabolism and/or sugar metabolism improver in the pharmaceutical composition or the food or beverage is not particularly limited as long as it imparts the improving effects of lipid metabolism and sugar metabolism, and is, depending on the preparation (or dosage) form, typically within the range of 0.0001 to 99% by mass, preferably 0.001 to 80% by mass, more preferably 0.001 to 75% by mass, in terms of the above bacterial cell or the treated product thereof, and it is desirable to prepare the improver into a form enabling control of a daily dose so that the suitable dose of active ingredient can be taken. Further, the bacterial cell or treated products thereof contained in the lipid metabolism and/or sugar metabolism improver of the present invention are those produced from the number of bacterial cells corresponding to, but not limited to, for example, about $10^5$ cells/g to about $10^{12}$ cells/g, preferably about $10^8$ cells/g to about $10^{12}$ cell/g, as the number of bacterial cell before treatment.

Other lipid metabolism improver and/or sugar metabolism improver can be added to or contained in the lipid metabolism and/or sugar metabolism improver of the present invention. The other lipid metabolism improver includes, but is not limited to, lipid depressants (e.g., statin drugs, fibrate drugs, eicosapentaenoic acid, docosahexaenoic acid, and the like), and vitamins (e.g., nicotinic acid, vitamin E, and the like). Further, the other sugar metabolism improver includes, but is not limited to, pioglitazone and the like.

Furthermore, the pharmaceutical composition or the food or beverage of the present invention may also contain various additives and other various substances used in the production thereof. Examples of such a substance and additive include various oils and fats (e.g., vegetable oils such as soybean oil, corn oil, safflower oil, olive oil, and the like, animal fats and oils such as beef tallow, sardine oil, and the like), crude drugs (e.g., royal jelly, ginseng, and the like), amino acids (e.g., glutamine, cysteine, leucine, arginine, and the like), polyhydric alcohols (e.g., ethylene glycol, polyethylene glycol, propylene glycol, glycerol, and sugar alcohols including sorbitol, erythritol, xylitol, maltitol, mannitol, and the like), natural polymers (e.g., gum arabic, agar, water-soluble corn fiber, gelatin, xanthan gum, casein, gluten or gluten hydrolyzate, lecithin, starch, dextrin, and the like), vitamins (e.g., vitamin C, vitamin B complex, and the like), minerals (e.g., calcium, magnesium, zinc, iron, and the like), dietary fibers (e.g., mannan, pectin, hemicellulose, and the like), surfactants (e.g., glycerol fatty acid esters, sorbitan fatty acid esters, and the like), purified water, excipients (e.g., glucose, cornstarch, lactose, dextrin, and the like), stabilizers, pH adjusting agents, antioxidants, sweeteners, taste components, acidulants, coloring agents, perfumes, and the like.

Furthermore, the lipid metabolism and/or sugar metabolism improver of the present invention may contain, as functional ingredients or additives other than the above active ingredients, for example, taurine, glutathione, carnitine, creatine, coenzyme Q, glucuronic acid, glucuronolactone, capsicium extract, ginger extract, cacao extract, guarana extract, garcinia extracts, theanine, γ-aminobutyric acid, capsaicin, capsiate, various organic acids, flavonoids, polyfenols, catechins, xanthine derivatives, non-digestible oligosaccharides such as fructooligosaccharide, and the like, polyvinylpyrrolidone, and the like.

The subjects (or patients) who are administered with or ingests the lipid metabolism improver and the pharmaceutical composition or food or beverage comprising the improver of the present invention are vertebrates, in particular, mammals such as human, primates (e.g., monkey, chimpanzee, and the like), livestock animals (e.g., cow, horse, pig, sheep, and the like), companion animals (e.g., dog, cat, and the like), experimental animals (e.g., mouse, rat, and the like), and further reptiles and birds, preferably human.

The dose or intake amount of the lipid metabolism and/or sugar metabolism improver of the present invention varies depending on the subject's age and body weight, administration or intake route, dose or intake frequency, severity of the lipid metabolism disorder or the like, and can be changed in a wide range by the discretion of a person skilled in the art to achieve the intended actions. For example, when orally administered or taken, the bacterial cell or the treated product thereof contained in the lipid metabolism and/or sugar metabolism improver is desirably administered in an amount of typically about $10^6$ cells to about $10^{12}$ cells, preferably about $10^7$ cells to about $10^{11}$ cells, per kg of body weight when represented by the bacterial cell amount before treatment.

The lipid metabolism and/or sugar metabolism improver, the pharmaceutical composition, and the food or beverage of the present invention are very safe and the intake amount can be increased. The daily intake amount may be taken once, or in several divided times. Additionally, the frequency of administration or intake is not particularly limited and can suitably be selected in accordance with various conditions such as administration or intake route, subject's age and body weight, the severity of lipid metabolism disorder or sugar metabolism disorder, the presence of disease or disorder onset caused by the lipid metabolism disorder or sugar metabolism disorder, intended effects (treatment, prevention, or the like), and the like.

The administration or intake route of the lipid metabolism and/or sugar metabolism improver, the pharmaceutical composition, and the food or beverage of the present invention includes, but is not particularly limited to, oral administration or intake, or parenteral administration (e.g., intrarectal, subcutaneous, intramuscular, and intravenous administrations), and the like, preferably oral administration or intake.

The lipid metabolism and/or sugar metabolism improver, the pharmaceutical composition, and the food or beverage of the present invention have the actions of reducing a subject's lipid in blood, promoting the metabolisms of subcutaneous fat and/or visceral fat, and suppressing the body weight gain, as the lipid metabolism improver. Specifically, the lipid metabolism improver, the pharmaceutical composition, and the food or beverage of the present invention have the effects of normalizing the lipid metabolism by reducing a subject's total cholesterol, LDL-cholesterol, triglyceride, arteriosclerotic index and/or visceral fat, and/or elevating HDL-cholesterol and/or adiponectin.

The lipid metabolism and/or sugar metabolism improver, the pharmaceutical composition, and the food or beverage of the present invention have the actions of preventing, improving, or treating diseases such as hyperglycemia, noninsulin dependent diabetes mellitus, or the like by improving the insulin resistance, as the sugar metabolism improver.

Accordingly, the lipid metabolism and/or sugar metabolism improver, the pharmaceutical composition, and the food or beverage of the present invention show good preventive, improving and therapeutic effects on the diseases or disorders associated with the lipid metabolism and sugar metabolism. In addition, they are very safe and easily taken continuously for an extended period of time.

In the present invention, the term "diseases or disorders associated with the lipid metabolism" refers to diseases, disorders, symptoms or syndromes caused by the lipid metabolism abnormality. Examples of the diseases or disorders associated with the lipid metabolism include, but are not limited to, arteriosclerosis, hyperlipidemia, steatohepatitis, obesity, metabolic syndrome, circulatory system diseases (e.g., myocardial infarction, cerebral infarction, and the like).

In the present invention, the term "diseases or disorders associated with the sugar metabolism" includes complications of diabetes mellitus such as dyslipidemia, hypertension, endodermal impairment, inflammatory atherosclerosis, and the like in addition to non-insulin-dependent diabetes mellitus and hyperglycemia.

The food or beverage of the present invention contains the lipid metabolism and/or sugar metabolism improver as described above. In the present invention, the food or beverage encompasses beverages. The food or beverage comprising the lipid metabolism and/or sugar metabolism improver of the present invention encompasses all foods or beverages to which the above lipid metabolism and/or sugar metabolism improver can be added, in addition to the health foods or beverages, functional foods or beverages, foods or beverages for specified health use, and the like, which enhance health by the lipid metabolism improving action and sugar metabolism improving action.

For the food or beverage comprising the lipid metabolism and/or sugar metabolism improver of the present invention, functional foods or beverages are particularly preferable. The "functional food or beverage" of the present invention means a food or beverage having a certain function on the living body, and encompasses the so-called health foods or beverages in general such as foods and beverages with health claims including foods and beverages for specified health use (including qualified "foods for specified health use") and foods and beverages with nutrient function claims, foods or beverages for special dietary uses, nutrition supplement foods or beverages, health supplement foods or beverages, supplements (e.g., those in various forms such as tablets, coated tablets, sugar coated tablets, capsules, solutions, or the like), food or beverage for beauty (e.g., diet food or beverage, and the like), and the like. The functional food or beverage of the present invention also encompasses the health foods or beverages to which the health claim based on the food standard by the Codex (the Joint FAO/WHO Food Standards Commission) is applicable.

Examples of foods or beverages include liquid foods such as intertubular enteral nutrients and the like; health foods or beverages and nutrition supplement foods or beverages in the form of preparation forms such as tablet candies, tablets, chewable tablets, dusts, powders, capsules, granules, drinks, and the like; tea drinks such as green teas, oolong tea, English teas, and the like; drinks such as soft drinks, jelly beverages, sports drinks, milk beverages, carbonated drinks, vegetable drinks, fruit juice drinks, fermented vegetable drinks, fermented fruit juice drinks, fermented milk beverages (yogurts and the like), lactic acid bacterial beverages, milk-based drinks (coffee-flavored milk, fruit-flavored milk, and the like), powder drinks, cocoa drinks, milk as well as purified water, and the like: spreads such as butter, jams, Furikake (dried food sprinkles), margarine, and the like; mayonnaise, shortening, custard cream, dressings, breads, rice, noodles, pastas, misosoup, soybean curd, yogurts, soups, sauces, confectioneries (e.g., biscuits, cookies, chocolates, candies, cakes, ice creams, chewing gums, tablets), and the like.

The food or beverage of the present invention can contain other food materials used in the production of the food or beverage, various nutrients, various vitamins, minerals, dietary fibers, various additives (e.g., taste components, sweeteners, acidulants such as organic acids, stabilizers, flavors) or the like, in addition to the above lipid metabolism and/or sugar metabolism improver, and can be produced in accordance with a routine method.

In the food or beverage of the present invention, the addition amount of lipid metabolism and/or sugar metabolism improver can suitably be determined by those skilled in the art in consideration with the preparation form and required flavors or textures of the food or beverage. Typically, the addition amount of the lipid metabolism and/or sugar metabolism improver is suitable when the total amount of the bacterial cell or the treated product thereof to be added to the lipid metabolism and/or sugar metabolism improver is typically 0.0001 to 99% by mass, preferably 0.001 to 80% by mass, more preferably 0.001 to 75% by mass, when represented by the bacterial cell amount before treatment. The lipid metabolism and/or sugar metabolism improver of the present invention is very safe and hence the addition amount to the food or beverage can further be increased. It is preferable to prepare the improver into a form enabling control of a daily dose so that the desirable intake amount of the lipid metabolism and/or sugar metabolism improver can be consumed. Thus, a prevention method and improving method for the diseases or disorders associated with the lipid metabolism and/or sugar metabolism using the food or beverage of the present invention are provided, when the food or beverage of the present invention is consumed in the form which enables control of the desirable intake amount of the lipid metabolism and/or sugar metabolism improver of the present invention.

The lipid metabolism and/or sugar metabolism improver of the present invention may be contained in foods or beverages by any suitable method available to those skilled in the art. For example, the lipid metabolism and/or sugar metabolism improver of the present invention is formulated into a liquid, gel, solid, powder or granular preparation, and subsequently added to a food or beverage. Alternatively, the lipid metabolism and/or sugar metabolism improver of the present invention may be directly mixed with or dissolved in raw materials of the food or beverage. The lipid metabolism and/or sugar metabolism improver of the present invention may be coated on, covered over, infiltrated into, or sprayed onto a food or beverage. The lipid metabolism and/or sugar metabolism improver of the present invention may be homogeneously dispersed or unevenly distributed in a food or beverage. A capsule comprising the lipid metabolism and/or sugar metabolism improver of the present invention may be prepared. The lipid metabolism and/or sugar metabolism improver of the present invention may be enveloped with an edible film, edible coating agent, or the like. Further, the lipid metabolism and/or sugar metabolism improver of the present invention may be molded to the shape of tablets or the like after adding a suitable excipient or the like. The food or beverage comprising the lipid metabolism and/or sugar metabolism improver of the present invention may further be processed, and such a processed product is also encompassed in the scope of the present invention.

Various additives routinely used in foods and beverages may be used in the production of the food or beverage of the present invention. The additives include, but are not limited to, color formers (sodium nitrite and the like), coloring agents (gardenia pigment, red 102, and the like), perfumes (orange perfume and the like), sweeteners (stevia, aspartame, and the like), preservatives (sodium acetate, sorbic acid, and the like), emulsifiers (sodium chondroitin sulfate, propylene glycol fatty acid esters, and the like), antioxidants (disodium EDTA, vitamin C, and the like), pH adjusting agents (citric acid and the like), synthetic seasonings (sodium inosinate and the like), thickeners (xanthan gum and the like), raising agents (calcium carbonate and the like), defoaming agents (calcium phosphate), and the like, binders (sodium polyphosphate and the like), nutrient enrichments (calcium fortifiers, vitamin A, and the like), excipients (water-soluble dextrin and the like), and the like. Further, functional materials such as Asian ginseng extract, Siberian ginseng extract, eucalyptus extract, gutta percha tea extract, or the like, may further be added thereto.

The food or beverage of the present invention, as described above, has the lipid metabolism and sugar metabolism improving actions, and thus has good preventing and improving actions on the diseases or disorders associated with the lipid metabolism and sugar metabolism and is very safe without concerns of adverse effects. Further, the lipid metabolism and/or sugar metabolism improver of the present invention has good flavor and does not affect flavors of any foods or drinks when added to various foods or drinks, and for this reason the obtained food or beverage can be easily taken continuously for an extended period of time and expected to have good preventing and improving effects on the diseases or disorders associated with the lipid metabolism.

Further, the lipid metabolism and/or sugar metabolism improver of the present invention can be added not only to foods or drinks for human consumption but also to feeds for livestock, racehorses, companion animals, and the like. The above descriptions on the food or beverage are equally applicable to the feed, since the feed is substantially the same as the food or beverage except that it is for other than human consumption.

EXAMPLES

Hereinafter, the present invention is further specifically described with reference to Examples, but is not limited thereto.

Example 1

<Production of Bacterial Cell Powder>

The cell strain of each lactic acid bacterium was inoculated from frozen stocks onto plate medium, and then the pre-preincubation, preincubation and main incubation were carried out (5 ml→40 ml→2 L) using liquid medium. Table 1 shows the bacterial species, bacterial strains, medium and incubation temperatures used. Additionally, the inoculum concentration was 1% of each liquid medium weight and the incubation was carried out for 18 hours (see Table 2 for the medium used and incubation temperatures). After the incubation, the culture was centrifuged at 12000 g at 10° C. for 7 minutes, and the supernatant was removed. Ion exchange water was added, the culture was centrifuged in the same manner, and the freeze-dried bacterial cell was dispersed using a mill (TESCOM), thereby obtaining a bacterial cell powder.

TABLE 1

| Bacterial species name | Bacterial strain No. | Culture temperature | Plate medium | Liquid medium |
|---|---|---|---|---|
| Enterococcus faecalis | 1 | 37 | MRS | MRS |
| Lactobacillus gallinarum | 2 | 37 | MRS | MRS |
| Lactobacillus delbrueckii | 3 | 37 | MRS | MRS |
| Lactobacillus johnsonii | 4 | 37 | MRS | MRS |
| Lactobacillus crispatus | 5 | 37 | MRS | MRS |
| Lactobacillus amylovorus | CP1563 | 37 | MRS | MRS |
| Lactobacillus amylovorus | 6 | 37 | MRS | MRS |
| Lactobacillus amylovorus | 7 | 37 | MRS | MRS |
| Lactobacillus amylovorus | ATCC33620 | 37 | MRS | MRS |
| Lactobacillus amylovorus | CP1562 | 37 | MRS | MRS |
| Lactobacillus acidophilus | 8 | 37 | MRS | MRS |
| Lactobacillus salivarius | 9 | 37 | MRS | MRS |
| Lactobacillus brevis | 10 | 37 | MRS | MRS |
| Lactobacillus coryniformis | 11 | 37 | MRS | MRS |
| Lactobacillus homohiochii | 12 | 37 | MRS | MRS |
| Lactobacillus buchneri | 13 | 37 | MRS | MRS |
| Lactobacillus gasseri | CP2305 | 37 | MRS | MRS |
| Lactococcus lactis | 14 | 30 | MRS | MRS |
| Leuconostoc lactis | 15 | 25 | MRS | MRS |
| Lactobacillus paracasei | 16 | 37 | MRS | MRS |
| Lactobacillus parakefir | 17 | 37 | BL | GAM |

TABLE 1-continued

| Bacterial species name | Bacterial strain No. | Culture temperature | Plate medium | Liquid medium |
|---|---|---|---|---|
| Lactobacillus plantarum | 18 | 37 | BL | GAM |
| Lactobacillus helveticus | 19 | 37 | ATCC | ATCC |
| Bifidobacterium adolescentis | 20 | 37 | BL | GAM |
| Bifidobacterium longum | 21 | 37 | BL | GAM |
| Bifidobacterium breve | 22 | 37 | BL | GAM |
| Bifidobacterium infantis | 23 | 37 | BL | GAM |
| Bifidobacterium catenulatum | 24 | 37 | BL | GAM |
| Bifidobacterium bifidum | 25 | 37 | BL | GAM |

(Preparation of Diethyl Ether Extract)

Two g of the bacterial cell powder was suspended in 500 ml of a 0.5 mol/l potassium hydroxide-ethanol solution (KANTO KAGAKU) and then disrupted ultrasonically for 2 minutes (power output 40%, max 750 W, probe-type, VC-750 (TOKYO RIKAKIKAI CO., LTD.)). The treated solution was transferred to a 500 ml wide mouthed medium bottle with a red cap (heat resistance, SANSYO), which was then hermetically closed. The bottle was heated in boiling water at 100° C. for 1 hour in the stationary state, and then cooled in running water. Concentrated hydrochloric acid (WAKO PURE CHEMICAL INDUSTRY, Ltd.) was added to the cooled bacterial solution to adjust pH to be 2 or less.

The liquid part was concentrated to about 50 ml in a water bath at 40° C. using a rotary evaporator (NVC-2100, TOKYO RIKAKIKAI CO., LTD.). The concentrated liquid was divided into two equal amounts, respectively placed in a 50 ml glass centrifuge tube (AGC Techno Glass, Co., Ltd.), diethyl ether (Wako Pure Chemical Industry, Ltd.) of the equal amount was added thereto and stirred for 1 hour using a shaker (200 rpm/min, R-30, TIETECH Co., Ltd.), thereby separating and collecting the upper layer. The same procedure was carried out 4 times in total, and the fraction separated and collected was dried to solidify using a rotary evaporator. The fraction was thoroughly dried to solidify by spraying nitrogen gas, then dissolved in 500 L of a special grade DMSO (WAKO PURE CHEMICAL INDUSTRY, Ltd.) and preserved at −80° C. in a brown vial (cold resistance, SANSYO). The fatty acid concentration in diethyl ether was measured using NEFA C-Test Wako (WAKO PURE CHEMICAL INDUSTRY, Ltd.).

Example 2

<PPARα Reporter Assay>

Cultured cell CV-1 derived from the kidney of an African green monkey was prepared to a concentration of $5 \times 10^4$ cells/ml, suspended in DMEM medium containing 10% (v/v) FBS (SIGMA), and cultured at 37° C. for 24 hours under 5% $CO_2$ in air (v/v) in a concentration of 500 μL/well using a flat 24-well plate (Corning). Twenty four hours later, 80 to 90% confluence was microscopically confirmed to have reached, and subsequently the transfection was carried out by the following procedure.

Plasmid pM-PPARα 0.16 μg, which comprises a DNA fragment encoding a chimeric protein comprising PPARα ligand binding domain (derived from human) and GAL-4DNA binding domain (derived from yeast), and p4xUASg-tk-luc 0.16 μg, which is a luc (derived from sea-firefly) reporter gene plasmid designed to receive expression control by the above chimeric protein, and pRL-CMV 0.016 μg, which is a luc (derived from Renilla) expression plasmid having a viral expression promoter with a fixed expression amount in cells, were added to 25 μl of the reduced serum medium Opti-MEM (Invitrogen) and mixed, to which 4 μl of PLUS Reagent (Invitrogen) was added and allowed to stand at room temperature for 15 minutes. Further, Lipofectamine Reagent (Invitrogen) 1 μl and Opti-MEM 25 μl were added thereto, allowed to stand at room temperature for 15 minutes, and subsequently Opti-MEM 200 μl was added thereto. The obtained solution 250 μl was added to the cultured CV-1 cell washed with Opti-MEM and incubated at 37° C. for 3 hours. After incubation, the medium was discarded and 1 ml of DMEM medium containing 10% (v/v) FBS was added. (Definition 1: "Negative Control 0 of PPARα Activity and Positive Control 100 of PPARα Activity")

Evaluation samples were prepared as follows. The diethyl ether extract of each lactic acid bacterium was diluted with Opti-MEM so that the final concentration of DMSO is 0.1%. GW7647 (SIGMA) was used as the positive control and DMSO was used as the negative control of the PPARα ligand. The concentration of the lactic acid bacterium extract sample was 2.5 μM (in terms of fatty acid), and the concentration of GW7647 was 10 nM, at the time of assay.

Twenty four hours later from the transfection, the medium of CV-1 cells was sucked, 500 μl of each sample to be evaluated was added, and washed twice with 500 μl PBS 6 hours later. After sucking and discarding PBS, 100 μL each of Reporter Lysis 5× Buffer (Promega) diluted 5 times with water was added and the entire plate was cryopreserved in a freezer at −80° C.

The cryopreserved sample 30 μL was added to a 96-well white microplate (PerkinElmer), and the luminescence intensities (590 nm and 645 nm) were measured using Dual-Glo™ Luciferase Assay System (Promega), whereby the PPARα ligand ability was measured. The activity is shown in the relative value when the negative control is 0 and the positive control is 100.

(Results)

Table 2 shows the results.

Preferably, the PPARα activity value is 70 or more, more preferably 80 or more, 90 or more, 95 or more, 100 or more, 120 or more, 140 or more.

TABLE 2

| Evaluated sample | Bacterial strain No. | Activity |
|---|---|---|
| Negative control | — | 0 |
| Positive control | — | 100 |
| Lactobacillus amylovorus | CP1563 | 146.7 |
| Lactobacillus amylovorus | CP1562 | 97.9 |
| Lactobacillus gasseri | CP2305 | 94.2 |
| Lactococcus lactis | 14 | 87.7 |
| Lactobacillus amylovorus | ATCC33620 | 87.7 |
| Lactobacillus amylovorus | 7 | 83.3 |
| Bifidobacterium infantis | 23 | 78.0 |
| Lactobacillus amylovorus | 6 | 72.7 |
| Bifidobacterium adolescentis | 20 | 71.8 |
| Bifidobacterium breve | 22 | 70.1 |
| Lactobacillus acidophilus | 8 | 65.3 |
| Bifidobacterium longum | 21 | 60.5 |
| Lactobacillus salivarius | 9 | 55.2 |
| Lactobacillus crispatus | 5 | 53.8 |
| Lactobacillus gallinarum | 2 | 50.7 |
| Bifidobacterium catenulatum | 24 | 49.3 |
| Bifidobacterium bifidum | 25 | 47.3 |
| Lactobacillus johnsonii | 4 | 46.2 |
| Lactobacillus plantarum | 18 | 44.1 |
| Enterococcus faecalis | 1 | 43.5 |
| Lactobacillus delbrueckii | 3 | 43.2 |
| Lactobacillus paracasei | 16 | 34.8 |
| Lactobacillus helveticus | 19 | 32.5 |
| Leuconostoc lactis | 15 | 30.4 |
| Lactobacillus homohiochii | 12 | 30.2 |
| Lactobacillus parakefir | 17 | 26.8 |
| Lactobacillus brevis | 10 | 16.8 |

TABLE 2-continued

| Evaluated sample | Bacterial strain No. | Activity |
|---|---|---|
| Lactobacillus buchneri | 13 | 14.5 |
| Lactobacillus coryniformis | 11 | −6.1 |

The results shown in Table 2 reveal that the activation abilities are significantly different depending on the bacterial strain. Of these, *Lactobacillus amylovorus* CP1563 strain showed the strongest PPARα activation ability and was found to have the stronger activation ability than the positive control. Although Patent Document 5 (JP Patent Publication (Kokai) No. 2007-284360) described in the above PRIOR ART DOCUMENT reported that *Lactobacillus amylovoruses* ATCC 33620 strain (JCM1126) exhibited a higher activity than the positive control, in the present result the strain exhibited lower activity than the positive control and only about 60% activation ability compared with that of *Lactobacillus amylovorus* CP1563 strain. Further, even NCI9040 strain having the highest activity in Patent Document 5 (Japanese Patent Publication (Kokai) No. 2007-284360) shows only about 67% activation ability compared with that of *Lactobacillus amylovorus* CP1563 strain.

Example 3

<PPARγ Reporter Assay>

Cultured cell CV-1 derived from the kidney of an African green monkey was prepared to a concentration of 5×10$^4$ cells/ml, suspended in DMEM medium containing 10% (v/v) FBS (SIGMA), and cultured at 37° C. for 24 hours under 5% CO$_2$ in air (v/v) in a concentration of 500 μL/well using a flat 24-well plate (Corning). Twenty four hours later, 80 to 90% confluence was microscopically confirmed to have reached and subsequently the transfection was carried out by the following procedure.

Plasmid pM-PPARα 0.16 μg, which comprises a DNA fragment encoding a chimeric protein comprising PPARγ ligand binding domain (derived from human) and GAL-4DNA binding domain (derived from yeast), and p4xUASg-tk-luc 0.16 μg, which is a luc (derived from sea-firefly) reporter gene plasmid designed to receive expression control by the above chimeric protein, and pRL-CMV 0.016 μg, which is a luc (derived from Renilla) expression plasmid having a viral expression promoter with a fixed expression amount in cells, were added to 25 μl of reduced serum media Opti-MEM (Invitrogen) and mixed, to which 4 μl of PLUS Reagent (Invitrogen) was added and allowed to stand at room temperature for 15 minutes. Further, 1 μl of Lipofectamine Reagent (Invitrogen) and 25 μl of Opti-MEM were added thereto and mixed, allowed to stand at room temperature for 15 minutes, and subsequently Opti-MEM 200 μl was added thereto. The obtained solution 250 μl was added to the cultured CV-1 cell washed with Opti-MEM and incubated at 37° C. for 3 hours. After incubation, the medium was discarded and 1 ml of DMEM medium containing 10% (v/v) FBS was added.

Samples to be evaluated were prepared as follows. Of the lactic acid bacteria strains listed in Table 1, diethyl ether extracts of *Lactobacillus amylovorus* CP1563 strain, *Bifidobacterium infantis* Na. 23 strain, *Bifidobacterium breve* No. 22 strain, *Lactobacillus gasseri* CP2305 strain, *Bifidobacterium adolescentis* No. 20 strain, *Bifidobacterium catenulatum* No. 24 strain, *Lactococcus lactis* No. 14 strain and *Bifidobacterium longum* No. 21 strain, which were 8 bacterium strains having the comparatively high PPARα activation ability, were diluted with Opti-MEM so that the final concentration of DMSO was 0.1%.

(Definition 2: "Negative Control 0 of PPARγ Ligand Activity and Positive Control 100 of PPARγ Ligand Activity")

Troglitazone (Wako Pure Chemical Industry, Ltd.) was used as the positive control and DMSO was used as the negative control of the PPARγ ligand. The concentration of lactic acid bacterium extract sample was 2.5 μM (in terms of fatty acid) and the concentration of Troglitazone was 1 nM, at the time of assay.

Twenty four hours later from the transfection, the medium of CV-1 cells was sucked, 500 μl of each sample to be evaluated was added, and washed twice with 500 μl PBS 6 hours later. After sucking and discarding PBS, 100 μL each of Reporter Lysis 5× Buffer (Promega) diluted 5 times with water was added and the entire plate was cryopreserved in a freezer at −80° C.

The cryopreserved sample 30 μL was added to a 96-well white microplate (PerkinElmer), and the luminescence intensities (590 nm and 645 nm) were measured using Dual-Glo™ Luciferase Assay System (Promega), whereby the PPARγ ligand ability was measured. The activity is shown in the relative value when the negative control is 0 and the positive control is 100.

(Results)

Table 3 shows the results.

TABLE 3

| Evaluated sample | Bacterial strain No. | Activity |
|---|---|---|
| Negative control | — | 0 |
| Positive control | — | 100 |
| Lactobacillus amylovorus | CP1563 | 42.1 |
| Bifidobacterium infantis | 23 | 34.7 |
| Bifidobacterium breve | 22 | 14.2 |
| Lactobacillus gasseri | CP2305 | 6.5 |
| Bifidobacterium adolescentis | 20 | 3.7 |
| Bifidobacterium catenulatunn | 24 | −4.3 |
| Lactococcus lactis | 14 | −10.0 |
| Bifidobacterium longum | 21 | −13.3 |

The results shown in Table 3 indicate that the PPARγ activation ability was found in *Lactobacillus amylovorus* CP1563 strain, *Bifidobacterium infantis* No. 23 strain, *Bifidobacterium breve* No. 22 strain, *Lactobacillus gasseri* CP2305 strain and *Bifidobacterium adolescentis* No. 20 strain. Of these, *Lactobacillus amylovorus* CP1563 strain showed the strongest PPARγ activation ability.

Further, as with *Lactoccus lactis* No. 14 strain, some bacterial strains with a comparatively high PPARα activity do not have the PPARγ activity. Accordingly, the fact that some bacteria such as *Lactobacillus amylovorus* CP1563 strain according to the present invention activate both PPARα and PPARγ is a remarkable finding.

Example 4

<Lipid Metabolism Improvement by CP1563 Strain (Mouse Test)>

The lactic acid bacterium, *Lactobacillus amylovorus* CP1563 strain (FERM BP-11255), was prepared as follows.

*Lactobacillus amylovorus* CP1563 strain was taken and isolated from human feces. The bacterial species was identified by the 16S rDNA nucleotide sequence analysis and phenotype observation.

The thus obtained bacterial strain was internationally deposited with the National Institute of Advanced Industrial Science and Technology, International Patent Organism Depositary (1-1-1 Higashi, Tsukuba, Ibaraki, Tsukuba Central 6 (305-8566 Japan)) on May 25, 2010 under the Budapest Treaty and given the accession number "FERM BP-11255".

The lactic acid bacterium was incubated at 37° C. for 18 hours using self-prepared food grade lactic acid bacterium medium and collected by centrifugal separation. After washing with deionized water and collecting, the cells were suspended again in a suitable amount of water and sterilized at 90° C. The sterilized suspension was disrupted using a DYNO-MILL under the following conditions.

Device used: DYNO-MILL Disruptor (Multi-Lab 0.6L, SHINMARU ENTERPRISES CORPORATION)
 Circumferential speed: 14.0 m/s
 Processing flow rate: 1 L/10 min
 Number of processing: 5 times
 Disrupting tank temperature: 15° C.
 Glass bead used: diameter 0.5 mm, 0.4 L The average major axis of destructed bacterial cells in the lactic acid bacterium suspension was reduced to 68% of before treatment (2.77μ→1.89 μm) by the above disruption (or destruction) treatment. After disruption, the suspension was freeze-dried, thereby obtaining a disrupted lactic acid bacterium freeze-dried powder.

In the present Example, the effects and dose dependency of lactic acid bacteria to a diet induced obese model mice were examined.

First, the ingredients were mixed in the amounts indicated in Table 4 to produce lactic acid bacterium containing high fat diets.

Figure 2:
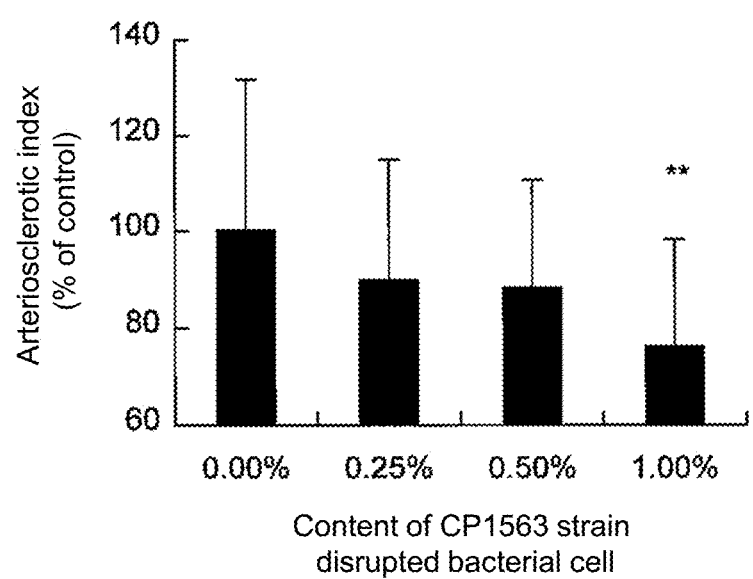
FIG. 2 is a graph showing a dose dependent effect (on arteriosclerotic index) of a lactic acid bacterium in diet induced obese model. ** shows the statistical significance.

The results are shown in FIG. 1 (HDL-cholesterol) and FIG. 2 (arteriosclerotic index). It was verified that the HDL-cholesterol and arteriosclerotic index were improved by administration of CP1563 strain disrupted bacterial cell and the effect was dose dependent.

Furthermore, the anti-metabolic syndrome effect of lactic acid bacteria on the diet induced obese model mice was investigated.

Specifically, the above obese model mice were fed with the *Lactobacillus amylovorus* CP1563 strain disrupted bacterial cell containing high fat diet (containing 0% or 1%, by weight) for 3 months. Then, the obese model mice were measured for HDL-cholesterol, LDL-cholesterol, triglyceride, arteriosclerotic index, high molecular adiponectin, and visceral fat weight.

Figure 3:
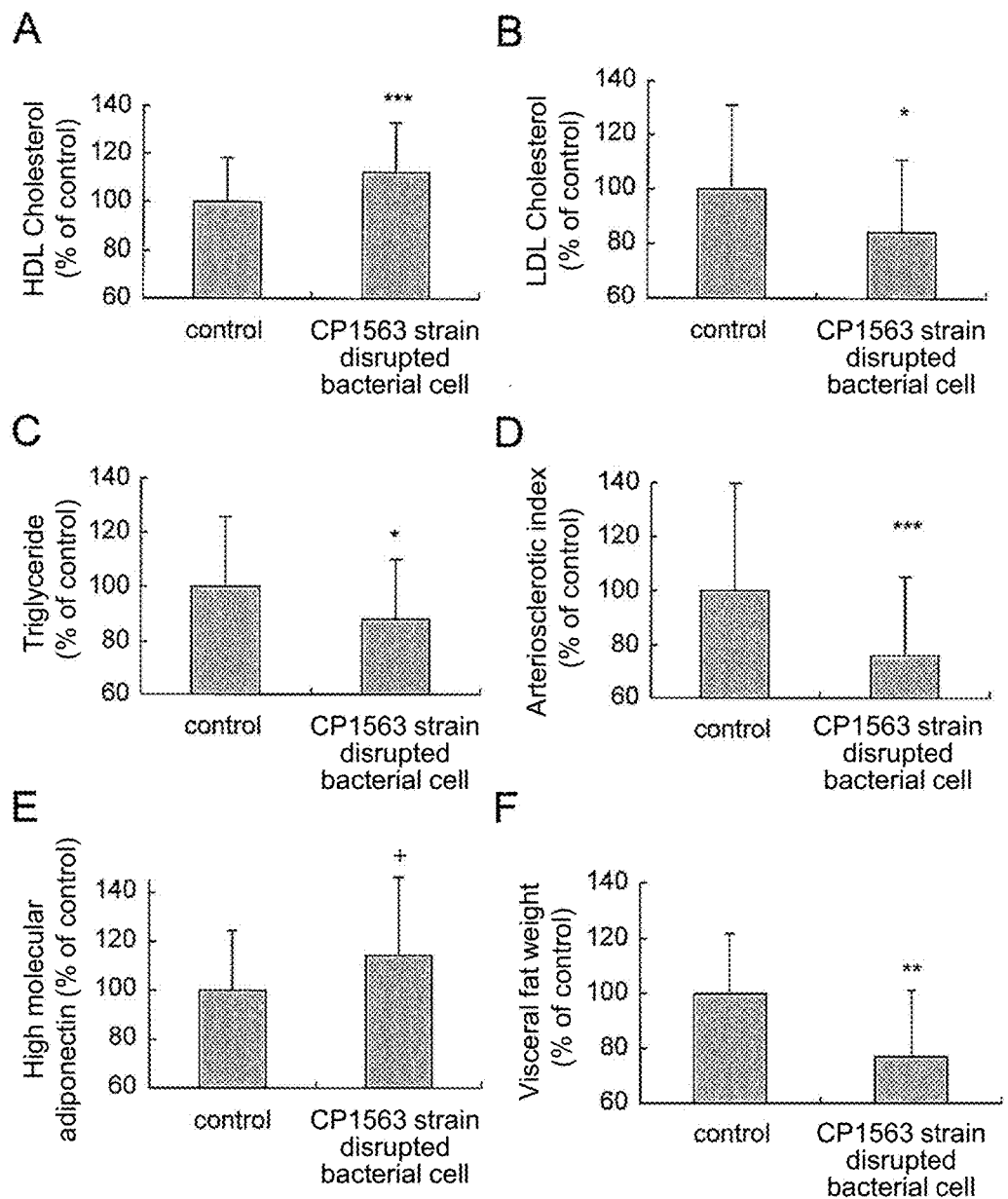
FIG. 3 is a graph showing an antimetabolic syndrome effect of a lactic acid bacterium in diet induced obese model. A is for HDL-cholesterol, B is for LDL-cholesterol, C is for triglyceride, D is for arteriosclerotic index, E is for high molecular adiponectin, and F is for visceral fat weight, respectively. *, , * and + show the statistical significance.

The results are shown in FIGS. 3, A to F. As shown in FIGS. 3, B, C, D and F, LDL-cholesterol, triglyceride, arteriosclerotic index and visceral fat weight were significantly reduced by administration of CP1563 strain disrupted bacterial cell. Further, HDL-cholesterol and high molecular adiponectin were significantly increased by administration of CP1563 strain disrupted bacterial cell. Consequently, the lipid metabolism of the obese model mice was significantly improved by administering the disrupted product of lactic acid bacteria.

Example 5

<Lipid Metabolism Improvement by CP1563 Strain (Validation of the Efficacy on Human)>

To validate the influence of disrupted bacterial cell of *Lactobacillus amylovorus* CP1563 strain to the lipid-relating

TABLE 4

| Ingredient name | Weight % | | | |
|---|---|---|---|---|
| | Control | 0.25% Lactic acid bacterium contained | 0.5% Lactic acid bacterium contained | 1.0% Lactic acid bacterium contained |
| Butter | 15.00 | 15.00 | 15.00 | 15.00 |
| Sucrose | 52.45 | 52.45 | 52.45 | 52.45 |
| Casein | 20.00 | 20.00 | 20.00 | 20.00 |
| Corn oil | 1.00 | 1.00 | 1.00 | 1.00 |
| Cellulose | 5.00 | 4.75 | 4.50 | 4.00 |
| Mineral mixture | 3.50 | 3.50 | 3.50 | 3.50 |
| Vitamin mixture | 1.00 | 1.00 | 1.00 | 1.00 |
| Choline chloride | 0.25 | 0.25 | 0.25 | 0.25 |
| Cystine | 0.30 | 0.30 | 0.30 | 0.30 |
| Cholesterol | 1.00 | 1.00 | 1.00 | 1.00 |
| Sodium cholate | 0.50 | 0.50 | 0.50 | 0.50 |
| Lactic acid bacterium freeze-dried powder | 0.00 | 0.25 | 0.50 | 1.00 |
| Lactic acid bacterium organic solvent extract | 0.00 | 0.00 | 0.00 | 0.00 |

C57BL/6 male mice (5 weeks of age) were fed with the high fat diet (control diet) prepared as above for 1 week before examination and used as obese model mice. Subsequently, the mice were fed with the *Lactobacillus amylovorus* CP1563 strain disrupted bacterial cell containing high fat diet (containing 0%, 0.25%, 0.5% or 1.0%, by weight) for 6 weeks. The mice were kept by the pair feeding method to adjust the food intake amount of each group to be equal. Blood samples were collected at the completion of experiment, and HDL cholesterol value was measured to investigate the effect of lactic acid bacteria. In addition, the arteriosclerotic index was determined by the following formula:

Arteriosclerotic index=(total cholesterol−HDL cholesterol)÷HDL cholesterol markers such as HDL cholesterol and the like, and visceral fat, a 12-week intake test was carried out. The test was a double blind parallel-group comparative study and carried out in conformity with the ethical principles of the Declaration of Helsinki.

CP1563 strain was cultured at 37° C. for 18 hours using self-prepared food grade lactic acid bacterium medium and collected by the filter concentration. The concentrated liquid was sterilized at 90° C. and freeze-dried, thereby obtaining a lactic acid bacterium freeze-dried powder. The bacterial cell was disrupted using a planetary ball mill under the following conditions.

Devise used: Planetary ball mill (SKF-04, SEISHIN ENTERPRISE Co., Ltd.)

Circumferential speed: 14.0 m/s
Ingredient feed amount: 200 g feed/pot
Media used: φ2 (3 kg/pot)
Number of rotations: 110 rpm (both the pot and table)
Disruption time: 10 hours The CP1563 strain disrupted bacterial cell whose average major axis was reduced to 47% of before treatment (2.77μ→1.30 μm) was obtained by the above disruption (destruction) treatment.

Forty male or female adult volunteers, having an HLD cholesterol of 40 mg/dL or less and a BMI of 28 or higher, were randomly assigned to 2 groups and asked to take 2 capsules each containing 100 mg of CP1563 strain disrupted bacterial cell or those not containing such a bacterial cell a day with water before or during breakfast for 12 weeks. Table 5 shows the formulation of the capsule.

TABLE 5

| Formulation | Ingredient (per capsule) | |
|---|---|---|
| | Control food | Test food |
| L. amylovorus CP1563 strain disrupted bacterial cell | 0 mg | 100 mg |
| Nisshoku Cornstarch IPW | 127 mg | 127 mg |
| Pinedex #2AG | 223 mg | 123 mg |
| Gelatin capsule (white No. 1) | 77 mg | 77 mg |
| Total | 427 mg | 427 mg |

Diagnose and physical examination were carried out 0, 8 and 12 weeks later from the intake, and the fat measurement by a CT scan was carried out 0 and 12 weeks later from the intake.

Figure 4:
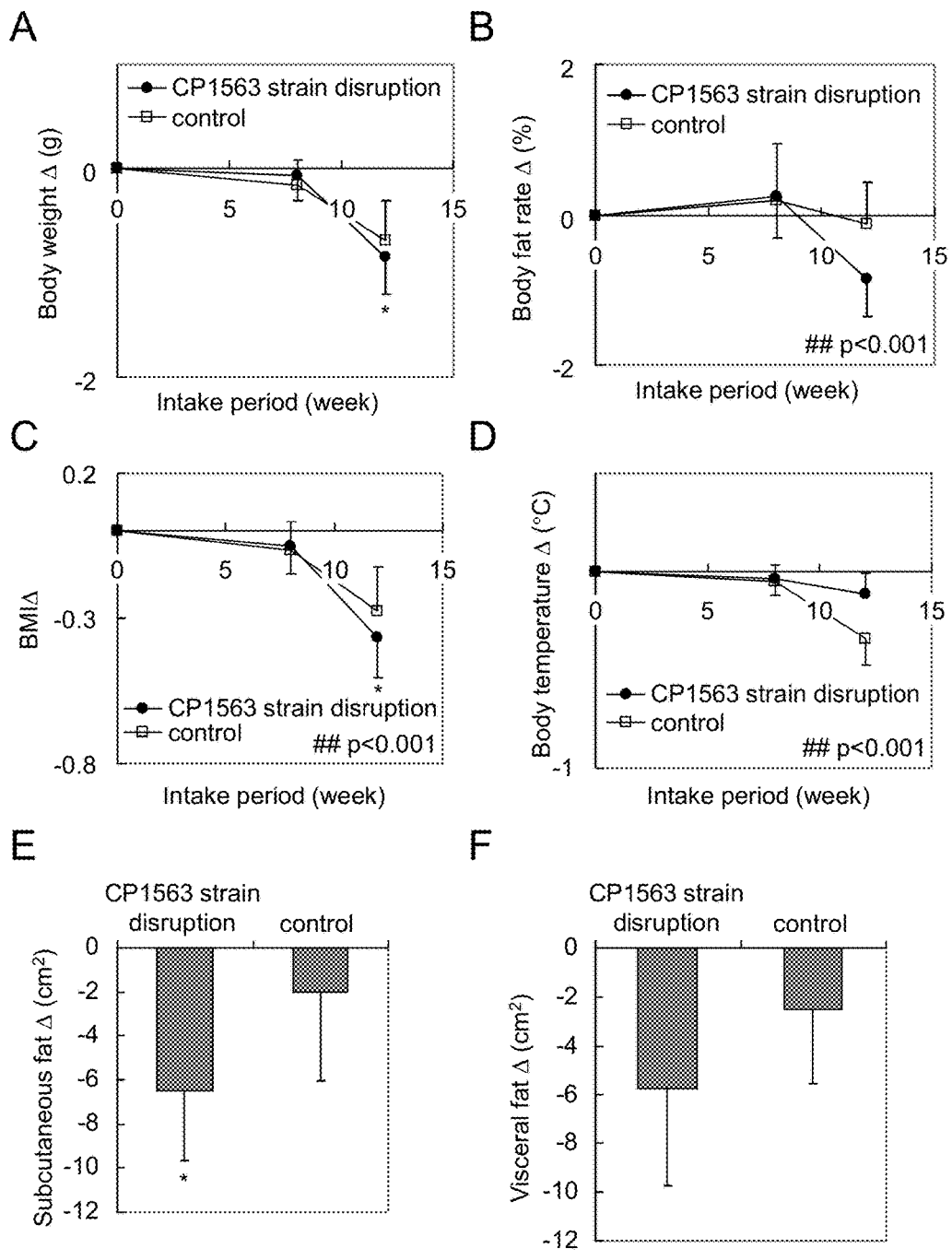
FIG. 4 is a graph showing the fat metabolism improving effect when the disrupted cells of *Lactobacillus amylovorus* CP1563 strain were administered to healthy human volunteers. The comparative control did not contain the disrupted cells of CP1563 strain. The influences to or effects on A: body weight, B: body fat ratio, C: BMI, D: body temperature, E: subcutaneous fat, and F: visceral fat, respectively, are shown.

The results are shown in FIG. 4, A to F. As shown in FIGS. 4, A, B, C and D, the body weight and BMI were significantly reduced when compared with before the intake by the administration of CP1563 strain disrupted bacterial cell, and the body fat rate and BMI were significantly reduced compared with the control groups (FIGS. 4B, 4C). Further, the body temperature was significantly reduced and suppressed when compared with the control groups (FIG. 4D). In addition, as shown in FIG. 4E, the subcutaneous fat area was significantly reduced when compared with before initiating the intake by the administration of the CP1563 strain disrupted bacterial cell. Furthermore, 31 human subjects with visceral fat-type obese, who had a visceral fat area of 100 $cm^2$ or more at the time of initiating the intake, were examined for the changed value of visceral fat amount, the visceral fat reduction amount was high in the CP1563 strain disrupted bacterial cell administered group as shown in FIG. 4F. Accordingly, it is verified that the physical examination values such as body weight, BMI, body fat rate, and the like, were improved, and the subcutaneous fat amount and visceral fat mount were reduced in a statistically significant manner.

Consequently, it is confirmed that the bacterial cells described herein can be used as the bacterial cell to produce the composition for improving the lipid metabolism and/or sugar metabolism. Further, it is confirmed that the bacterial cells described herein can be used as the bacterial cell to produce the composition for improving or preventing the lipid metabolism and/or sugar metabolism.

Further, it is confirmed that the bacterial cells described herein can be used as the bacterial cell to produce the composition for reducing the subcutaneous fat and/or visceral fat, and can be used as the bacterial cell to produce the composition for preventing the subcutaneous accumulation of fat and/or visceral fat.

For reference, the measurement method in the above physical examination was described below in detail.

At the time of visiting the hospital 0, 8 and 12 weeks later from the intake, the human subjects did not eat any food or drink other than water since 21 pm on the previous night and measured in the morning at the hospital.

(Body Weight and Body Fat Ratio Measurement)

Tanita body fat analyzer TBF-310 was used for the measurement.

(Fat Measurements by CT Scan)

For the CT scan, the CT scanner system (CT-W450) of Hitachi Medical Corporation was used.

Device setup:
Tube voltage; 12 kVp
mAs value; 90 mAs
Window level; 0
Window width; 1000

Process for taking images: the following (a) to (i) were carried out in the sequential order.

(a) A human subject was asked to put on a hospital gown in advance and lie down on the back on a platform with both arms up.

(b) The platform was moved close to the position where images were taken.

(c) The umbilical region was exposed and the position to be scanned was adjusted by a slit lamp (light localizer).

(d) The human subject was asked to practice how to breathe 2 to 3 times for the time of CT scanning.

(e) The final position to be scanned was adjusted while checking the lamp by moving the platform upward and downward.

(f) An image was taken at the central part of the navel on a manual mode.

(g) Subsequently, 3 sequential images at the central part of the navel and 3 mm above and below parts therefrom were taken from the same position on an automatic mode.

(h) The 3 images taken were studied and one closest to the central part of the navel was saved. When any image was left from the previous measurement, the one having the measurement position close to the previous image was used.

(i) The visceral fat area and subcutaneous fat area were calculated using a visceral fat measurement PC software (Fat Scan™ Ver. 3.0, N2 System Corp.).

Attention During the Examination:

(1) The human subjects were instructed not to eat meals containing a large amount of oligosaccharides and dietary fiber and not to drink a carbonated beverage as possible on the day before the examination.

(2) The human subjects were instructed not to put on any shapewear such as girdles, body suits, or the like, on the examination day.

(3) When in a hospital gown, the human subjects were allowed to keep only the underpants underneath the gown regardless of sex and asked to pull down the underpants to keep them away from the navel. When any underwear lines left from fastening around the abdominal area are found, the waist area was massaged.

(4) When the human subject lied down on the back on the platform for the scan, the posture was corrected to be straight.

(5) Before adjusting the position, the hip of the human subject was lifted several times so that the skin was not pulled to the platform.

(6) To scan the navel part when exhaled, the position was adjusted by allowing the subject to practice how to breathe with the light showing the position to be scanned directed thereon.

(7) When any image was left from the previous measurement, the position to be scanned was determined with reference to the previous images on a monitor.

INDUSTRIAL APPLICABILITY

The lipid metabolism and/or sugar metabolism improver of the present invention can improve the lipid metabolism and/or sugar metabolism on the human test, and is hence useful for preventing, improving or treating the diseases or disorders associated with such metabolism abnormalities. Specifically, the present invention provides the lactic acid bacterium, Lactobacillus amylovorus CP1563 strain, which has not only high PPARα activation ability but also high PPARγ activation ability. The lactic acid bacteria of the present invention promote the fat burning by the PPARα activation and increase the expression of adiponectin, which is a beneficial factor secreted from the fat cells by the PPARγ activation, and thus they can be used for preventing or treating various diseases or disorders. Consequently, the present invention is useful in the fields of pharmaceutical products, food or beverages, livestock farming, and the like.

All publications, patents and patent applications quoted herein are intended to be incorporated herein by reference in their entirety.

The Accession Numbers of the microorganisms used herein are as follows.

"FERM BP-11255" is the accession number for Lactobacillus amylovorus CP1563 strain internationally deposited with the National Institute of Advanced Industrial Science and Technology, International Patent Organism Depositary (1-1-1 Higashi, Tsukuba, Ibaraki, Tsukuba Central 6 (305-8566 Japan)) on May 25, 2010 under the Budapest Treaty, "FERM BP-11379" is the accession number for Lactobacillus amylovorus CP1562 strain internationally deposited with the National Institute of Advanced Industrial Science and Technology, International Patent Organism Depositary (1-1-1 Higashi, Tsukuba, Ibaraki, Tsukuba Central 6 (305-8566 Japan)) on Apr. 22, 2011 under the Budapest Treaty, and "FERM BP-11331" is the accession number for Lactobacillus gasseri CP2305 strain internationally deposited with the National Institute of Advanced Industrial Science and Technology, International Patent Organism Depositary (1-1-1 Higashi, Tsukuba, Ibaraki, Tsukuba Central 6 (305-8566 Japan)) on Sep. 11, 2007 under the Budapest Treaty.

The invention claimed is:

1. A method for improving lipid metabolism and/or sugar metabolism in a subject in need thereof, comprising administering an effective amount of a lactic acid producing bacterium, a treated product thereof, or a mixture thereof to the subject, thereby improving lipid metabolism and/or sugar metabolism in the subject,
wherein the effective amount corresponds to about $10^5$ cells/gram to about $10^{14}$ cells/gram of the lactic acid producing bacterium;
wherein the lactic acid producing bacterium is Lactobacillus amylovorus CP1563 strain (Accession Number FERM BP-11255), Lactobacillus amylovorus CP1562 strain (Accession Number FERM BP-11379), or a mutant or bred strain thereof;
wherein the lactic acid producing bacterium has dual-agonistic activities on a peroxisome proliferator activated receptor (PPAR)α and a peroxisome proliferator activated receptor (PPAR)γ, wherein
(a) the PPARα agonistic activity is about 70% or more of the PPARα agonistic activity of a positive control, as measured by a PPARα reporter assay; and
(b) the PPARγ agonistic activity is about 30% or more of the PPARγ agonistic activity of a positive control, as measured by a PPARγ reporter assay.

2. The method of claim 1, wherein the treated product is a destructed bacterial cell, extracted bacterial cell, frozen bacterial cell, emulsified bacterial cell, dried bacterial cell, or freeze-dried product thereof.

3. The method of claim 1, wherein the lactic acid producing bacterium, treated product thereof, or mixture thereof is in a form of a pharmaceutical composition, food, or beverage.

4. A method for improving, or treating a lipid metabolism disorder and/or sugar metabolism disorder in a subject in need thereof, comprising administering an effective amount of a lactic acid producing bacterium, a treated product thereof, or a mixture thereof to the subject, thereby improving, or treating the lipid metabolism disorder and/or sugar metabolism disorder in the subject,
wherein the effective amount corresponds to about $10^5$ cells/gram to about $10^{14}$ cells/gram of the lactic acid producing bacterium;
wherein the lactic acid producing bacterium is Lactobacillus amylovorus CP1563 strain (Accession Number FERM BP-11255), Lactobacillus amylovorus CP1562 strain (Accession Number FERM BP-11379), or a mutant or bred strain thereof;
wherein the lactic acid producing bacterium has dual-agonistic activities on a peroxisome proliferator activated receptor (PPAR)α and a peroxisome proliferator activated receptor (PPAR)γ, wherein
(a) the PPARα agonistic activity is about 70% or more of the PPARα agonistic activity of a positive control, as measured by a PPARα reporter assay; and
(b) the PPARγ agonistic activity is about 30% or more of the PPARγ agonistic activity of a positive control, as measured by a PPARγ reporter assay.

5. The method of claim 4, wherein the treated product is a destructed bacterial cell, extracted bacterial cell, frozen bacterial cell, emulsified bacterial cell, dried bacterial cell, or freeze-dried product thereof.

6. The method of claim 4, wherein the lactic acid producing bacterium, treated product thereof, or mixture thereof is in a form of a pharmaceutical composition, food, or beverage.

7. The method of claim 4, wherein the lipid metabolism disorder and/or sugar metabolism disorder is selected from the group consisting of: arteriosclerosis, hyperlipidemia, steatohepatitis, obesity, metabolic syndrome, circulatory system diseases including myocardial infarction and cerebral infarction, complications of diabetes mellitus including dyslipidemia, hypertension, endodermal impairment and inflammatory atherosclerosis, and non-insulin-dependent diabetes mellitus and hyperglycemia.

8. A method for reducing subcutaneous fat and/or visceral fat in a subject in need thereof, comprising administering an effective amount of a lactic acid producing bacterium, a treated product thereof, or a mixture thereof to the subject, thereby reducing subcutaneous fat and/or visceral fat in the subject,
wherein the effective amount corresponds to about $10^5$ cells/gram to about $10^{14}$ cells/gram of the lactic acid producing bacterium;

wherein the lactic acid producing bacterium is *Lactobacillus amylovorus* CP1563 strain (Accession Number FERM BP-11255), *Lactobacillus amylovorus* CP1562 strain (Accession Number FERM BP-11379), or a mutant or bred strain thereof;

wherein the lactic acid producing bacterium has dual-agonistic activities on a peroxisome proliferator activated receptor (PPAR)α and a peroxisome proliferator activated receptor (PPAR)γ, wherein (a) the PPARα agonistic activity is about 70% or more of the PPARα agonistic activity of a positive control, as measured by a PPARα reporter assay; and (b) the PPARγ agonistic activity is about 30% or more of the PPARγ agonistic activity of a positive control, as measured by a PPARγ reporter assay.

9. The method of claim 8, wherein the treated product is a destructed bacterial cell, extracted bacterial cell, frozen bacterial cell, emulsified bacterial cell, dried bacterial cell, or freeze-dried product thereof.

10. The method of claim 8, wherein the lactic acid producing bacterium, treated product thereof, or mixture thereof is in a form of a pharmaceutical composition, food, or beverage.

* * * * *